United States Patent
Cegelski et al.

(10) Patent No.: US 9,271,493 B2
(45) Date of Patent: Mar. 1, 2016

(54) METHODS FOR MICROBIAL BIOFILM DESTRUCTION

(71) Applicant: The Board of Trustees of the Leland Stanford Junior University, Palo Alto, CA (US)

(72) Inventors: Lynette Cegelski, Stanford, CA (US); Ji Youn Lim, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 13/921,916

(22) Filed: Jun. 19, 2013

(65) Prior Publication Data

US 2013/0338233 A1     Dec. 19, 2013

Related U.S. Application Data

(60) Provisional application No. 61/661,626, filed on Jun. 19, 2012.

(51) Int. Cl.
| | |
|---|---|
| *A01N 35/00* | (2006.01) |
| *A61K 31/12* | (2006.01) |
| *A01N 35/02* | (2006.01) |
| *A61K 45/06* | (2006.01) |

(52) U.S. Cl.
CPC .............. *A01N 35/02* (2013.01); *A61K 31/12* (2013.01); *A61K 45/06* (2013.01)

(58) Field of Classification Search
None
See application file for complete search history.

(56) References Cited

U.S. PATENT DOCUMENTS

2010/0266716 A1* 10/2010 Olson et al. .................... 424/756

OTHER PUBLICATIONS

Haukvik et al., A screening of curcumin derivatives for antibacterial phototoxic effects; Studies on curcumin and curcuminoids. XLIII, Pharmazie 66 (2011).*
Dovigo et al., "Investigation of the Photodynamic Effects of Curcumin Against Candida albicans," Photochemistry and Photobiology, 2011, 87:895-903.*
Uppuluri et al., "Characteristics of Candida albicans Biofilms Grown in a Synthetic Urine Medium," Journal of Clinical Microbiology, Dec. 2009, p. 4078-4083.*
Ferriéres et al., "Biofilm exclusion of uropathogenic bacteria by selected asymptomatic bacteriuria *Escherichia coli* strains," Microbiology (2007), 153, 1711-1719.*
Dovigo; et al. "Investigation of the Photodynamic Effects of Curcumin Against Candida albicans", Photochem Photobiol (Jul.-Aug. 2013), 87(4):895-903.
Hegge; et al. "Photoinactivation of *Staphylococcus epidermidis* biofilms and suspensions by the hydrophobic photosensitizer curcumin—effect of selected nanocarrier: studies on curcumin and curcuminoides XLVII", Eur J Pharm Sci (Aug. 2012), 47(1):65-74.
Moshe; et al. "Curcumin: a natural antibiofilm agent", Science & Technology Against Microbial Pathogens: The International Conference on Microbial Research (Nov. 2010), 89-93.
Orlando; et al. "A chemical analog of curcumin as an improved inhibitor of amyloid Abeta oligomerization", PLoS One (Mar. 2012), 7(3):e31869.
Pandit; et al. "Separation of an effective fraction from turmeric againstbiofilms by the comparison of curcuminoid content and anti-acidogenic activity", Food Chemistry (Dec. 2010), 1565-1570.
Pattiyathanee; et al. "Effect of curcumin on Helicobacter pylori biofilm formation", African Journal of Biotechnology (Oct. 2009), 8(19):5106-5115.
Ravindran; et al. "Bisdemethylcurcumin and structurally related hispolon analogues of curcumin exhibit enhanced prooxidant, antiproliferative and anti-inflammatory activities in vitro", Biochem Pharmacol (Jun. 2010), 79 (11):1658-1666.
Rudrappa; et al. "Curcumin, a Known Phenolic from Curcuma longa, Attenuates the Virulence of Pseudomonas aeruginosa PAO1 in Whole Plant and Animal Pathogenicity Models", J Agric Food Chem (Mar. 2008), 56 (6):1955-1962.
Song; et al. "Curcumin suppresses *Streptococcus mutans* adherence to human tooth surfaces and extracellular matrix proteins", Eur J Clin Microbiol Infect Dis (Jul. 2012), 31(7):1347-1352.

* cited by examiner

*Primary Examiner* — Craig Ricci
*Assistant Examiner* — Jared D Barsky
(74) *Attorney, Agent, or Firm* — Pamela J. Sherwood; Bozicevic, Field & Francis LLP

(57) ABSTRACT

Compositions and methods for the dissolution of a microbial biofilm are provided, where the method comprises contacting a microbiofilm with an effective dose of a curcumin derivative as a biofilm inhibitor. In some embodiments the curcumin derivative is dimethoxycurcumin. In some embodiments the biofilm comprises *E. coli*, e.g. including uropathogenic *E. coli*. The biofilm can be present in vitro or in vivo. The biofilm inhibitor may be administered alone, or in combination with bacteriocidal agents.

10 Claims, 4 Drawing Sheets
(3 of 4 Drawing Sheet(s) Filed in Color)

METHODS FOR MICROBIAL BIOFILM DESTRUCTION

GOVERNMENT RIGHTS

This invention was made with Government support under contract OD007488 awarded by the National Institutes of Health. The Government has certain rights in this invention.

BACKGROUND OF THE INVENTION

This era may come to be remembered as one in which infectious diseases made a dramatic worldwide resurgence, owing to the rise of antibiotic resistance and the dwindling and startlingly scarce number of candidate antibiotics in the drug development pipeline. Our current arsenal of antibiotics is comprised of variations on the single theme of cell killing, i.e. drugs that target processes essential to bacterial viability. Targeting bacterial virulence is an alternative and attractive approach to the development of new antimicrobials that can be used to disarm pathogens in the host, increase the number of available therapeutics, and protect the effectiveness of current antibiotics. The overall strategy is to inhibit specific mechanisms that promote infection and are essential to persistence in a pathogenic cascade, though not required for cell viability per se.

A biofilm is an accumulation of microorganisms (bacteria, fungi, and/or protozoa, with associated bacteriophages and other viruses) embedded in a polysaccharide matrix and adherent to solid biological or non-biotic surfaces. Biofilms are medically important, accounting for over 80 percent of hospital-acquired microbial infections in the body. Examples include infections of the: oral soft tissues, teeth and dental implants; middle ear; gastrointestinal tract; urogenital tract; airway/lung tissue; eye; urinary tract prostheses; peritoneal membrane and peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses, internal fixation devices, percutaneous sutures; and tracheal and ventilator tubing. The microorganisms tend to be far more resistant to antimicrobial agents and to be particularly difficult for the host immune system to render an appropriate response.

Biofilms are remarkably difficult to treat with antimicrobials. Antimicrobials may be readily inactivated or fail to penetrate into the biofilm. In addition, bacteria within biofilms have increased (up to 1000-fold higher) resistance to antimicrobial compounds, even though these same bacteria are sensitive to these agents if grown under planktonic conditions.

Biofilms play a significant role in the transmission and persistence of human disease and have emerged as virulence hallmarks of serious and persistent infectious diseases, including cystic fibrosis pneumonia, infective endocarditis, urinary tract infection (UTI), periodontitis, chronic infections of the middle ear, and infections of medical devices such as intravenous catheters and artificial joints. Currently available antibiotics often fail to eradicate biofilm-associated bacteria, necessitating multiple and intense antibiotic treatment regimens that drive the evolution of resistant pathogens and the exhaustion of last-resort antibiotics. As a consequence, biofilm-associated infections are the cause of significant morbidity and mortality in the clinic.

UTIs, which include infections of the bladder (cystitis) and kidney (pyelonephritis), are among the most common bacterial infections. Nearly 13 million women per year suffer from UTIs in the United States, and more than half of all women will experience a UTI during their lifetimes. A woman treated for an uncomplicated UTI has a 25-50% chance of developing a recurrent infection within one year of the primary infection and most are caused by the same bacterial strain as the initial infection. Furthermore, approximately one fourth of the yearly $4 billion cost attributed to nosocomial infections is a consequence of UTI, most of which are catheter-associated UTIs. Unfortunately, limited treatment options are available for patients with chronic and recurrent UTIs. These patients are typically given prolonged courses of antibiotics, which radically disrupt the symbiotic host microbiota and may be accompanied by the evolution of drug-resistant organisms in the urinary tract. In addition, UTIs have a strong causal correlation with systemic infection and sepsis if antibiotic therapy is ineffective.

Uropathogenic *Escherichia coli* (UPEC) are the most common etiologic agents, responsible for 80 to 85% of community-acquired UTIs. UPEC engage in a coordinated and regulated genetic and molecular pathogenic cascade that involves several distinct phases as examined in the mouse cystitis model and human UTIs. UPEC are thought to emerge primarily from the distal genitourinary tract and ascend the urethra into the bladder. UPEC bind to and invade the superficial umbrella cells that line the bladder lumen, where they rapidly replicate to form a biofilm-like intracellular bacterial community (IBC). In the IBC, bacteria find a safe haven where they are resistant to antibiotics, and subvert clearance by innate host responses. Even after acute infection is resolved, bacteria can persist within the bladder for many days to weeks, regardless of standard antibiotic treatments, and can be source of recurrent urinary tract infections. In the pathogenesis of catheter-associated UTI, UPEC form robust biofilms on urinary catheters and can serve as the pioneer pathogens to initiate the infectious cascade as well as more serious sequelae including bacteremia. Whether in the intracellular niche or on catheter surfaces, targeting UPEC biofilm formation has emerged as a ripe candidate for the development of anti-virulence therapeutics.

Several frank bacterial pathogens have been shown to associate with, and in some cases, grow in biofilms, including *Legionella pneumophila, S. aureus, Listeria monocytogenes, Campylobacter* spp., *E. coli* O157:H7, *Salmonella typhimurium, Vibrio cholerae*, and *Helicobacter pylori*. Although all these organisms have the ability to attach to surfaces and existing biofilms, most if not all appear incapable of extensive growth in the biofilm. This may be because of their fastidious growth requirements or because of their inability to compete with indigenous organisms. Survival and growth of pathogenic organisms within biofilms might also be enhanced by the association and metabolic interactions with indigenous organisms.

Bacteria embedded within biofilms are resistant to both immunological and non-specific defense mechanisms of the body. Contact with a solid surface triggers the expression of a panel of bacterial enzymes, which catalyze the formation of sticky polysaccharides that promote colonization and protection. The structure of biofilms is such that immune responses may be directed only at those antigens found on the outer surface of the biofilm, and antibodies and other serum or salivary proteins often fail to penetrate into the biofilm. In addition, phagocytes are unable to effectively engulf a bacterium growing within a complex polysaccharide matrix attached to a solid surface. This causes the phagocyte to release large amounts of pro-inflammatory enzymes and cytokines, leading to inflammation and destruction of nearby tissues.

In view of the importance of biofilms for microbial infection, methods of understanding and manipulating biofilm dissolution are of great interest, and are addressed herein.

Publications

Ravindran et al. (2010) Biochem Pharmacol. 79(11):1658-1666. Orlando et al. (2012) PLoS One 7(3):e31869. Moshe, SCIENCE AND TECHNOLOGY AGAINST MICROBIAL PATHOGENS Research, Development and Evaluation (pp 89-93), DOI No: 10.1142/9789814354868_0017.

Barnhart and Chapman (2006) Annu. Rev. Microbiol. 60:131-147; Romero et al. (2010) Proc. Natl. Acad. Sci. USA 107:2230-2234; Nenninger et al. (2009) Proc. Natl. Acad. Sci. USA 106:900-905; Cegelski et al. (2008) Nature Reviews Microbiology 6:17-27; Cegelski et al. (2009) Nat. Chem. Biol. 5:913-919.

SUMMARY OF THE INVENTION

Compositions and methods are provided for the dissolution of microbial biofilms. Chemical or biological means that interfere with amyloid formation induce biofilm dissolution, providing targets for a new class of antibiotics. In one embodiment of the invention, the biofilm inhibitor is a curcumin derivative, including without limitation dimethoxycurcumin.

In some embodiments, a method of dissolving a microbial biofilm is provided, where the method comprises contacting a microbiofilm with an effective dose of a curcumin derivative as a biofilm inhibitor. In some embodiments the curcumin derivative is dimethoxycurcumin. In some embodiments the biofilm comprises E. coli, e.g. including uropathogenic E. coli. In other embodiments the microbial film comprises, for example, uropathogenic and enterohemorrhagic microorganisms, e.g. E. coli, Salmonella species, etc. In some embodiments, the biofilm comprises a gram-positive organism, e.g. Staphylococcus aureus, etc. The biofilm can be present in vitro or in vivo. The biofilm inhibitor may be administered alone, or in combination with bacteriocidal agents, e.g. antibiotics, etc. The in vitro dissolution of biofilms can find use in hospital settings, and may be combined with other bacteriocidal agents. The curcumin derivatives are able to bind to curli extracellularly and inhibit biofilm extracellularly and therefore do not have to enter bacterial cells and are not subject to resistance mechanisms such as small-molecule efflux systems.

In some embodiments a pharmaceutical composition comprising a biofilm inhibitor of the invention as an active agent and a pharmaceutically acceptable excipient is provided. The formulation can be provided, for example, as a unit dose formulation, in a dose that is effective for dissolution of a microbial biofilm. The formulation may be administered to a patient suffering from a microbial infection, particularly bacterial infections forming or derived from biofilms.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
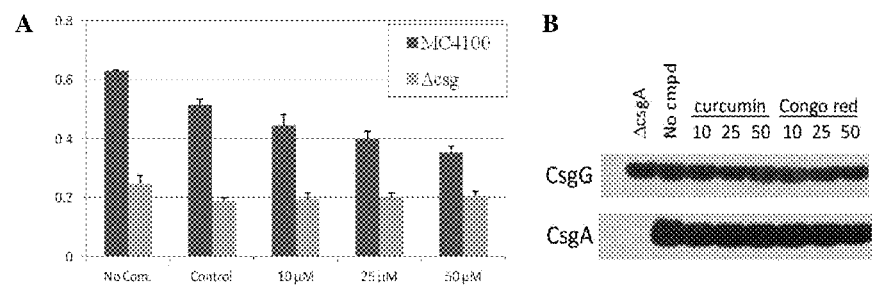
FIGS. 1A-1B. Bacteria growing under normal curli-producing conditions on agar in the presence of curcumin exhibited reduced adhesion to the protein fibronectin (A). Curcumin did not influence the production of curli proteins (B).

Methods are provided for the use of biofilm dissolving agents as antimicrobial agents. Such a biofilm inhibitor(s) can be administered alone or in combination with other active agents to a patient suffering from or predisposed to an infection comprising biofilm formation, in a dose and for a period of time sufficient to reduce the patient population of microbial pathogens. Such a biofilm inhibitor can also be used in contact with in vitro surfaces, including particularly medical surfaces. Specific treatments of interest include, without limitation, treatment of patients having implantable medical devices, which are particularly susceptible to biofilm formation; and in the treatment of infections with uropathogenic and enterohemorrhagic microorganisms, e.g. E. coli, Salmonella species, etc.

A biofilm is an assemblage of microbial cells that is closely associated with a surface and enclosed in a matrix of material, including polysaccharides, DNA, and proteins. Noncellular materials such as mineral crystals, corrosion particles, clay or silt particles, or blood components, depending on the environment in which the biofilm has developed, may also be found in the biofilm matrix. Biofilm-associated organisms also differ from their planktonic (freely suspended) counterparts with respect to the genes that are transcribed. Biofilms may form on a wide variety of surfaces, including living tissues, indwelling medical devices, industrial or potable water system piping, or natural aquatic systems.

The solid-liquid interface between a surface and an aqueous medium provides an ideal environment for the attachment and growth of microorganisms. The solid surface may have several characteristics that are important in the attachment process. The extent of microbial colonization appears to increase as the surface roughness increases. This is because shear forces are diminished, and surface area is higher on rougher surfaces. The physicochemical properties of the surface may also exert a strong influence on the rate and extent of attachment. Microorganisms attach more rapidly to hydrophobic, nonpolar surfaces such as Teflon and other plastics than to hydrophilic materials such as glass or metals.

Other characteristics of the aqueous medium, such as pH, nutrient levels, ionic strength, and temperature, may play a role in the rate of microbial attachment to a substratum. Several studies have shown a seasonal effect on bacterial attachment and biofilm formation in different aqueous systems. This effect may be due to water temperature or to other unmeasured, seasonally affected parameters.

Cell surface hydrophobicity, presence of fimbriae and flagella, and production of EPS all influence the rate and extent of attachment of microbial cells. The hydrophobicity of the cell surface is important in adhesion because hydrophobic interactions tend to increase with an increasing nonpolar nature of one or both surfaces involved (i.e., the microbial cell surface and the substratum surface). Most bacteria are negatively charged but still contain hydrophobic surface components. Fimbriae, i.e., nonflagellar appendages other than those involved in transfer of viral or bacterial nucleic acids, contribute to cell surface hydrophobicity. Most fimbriae that have been examined contain a high proportion of hydrophobic amino acid residues. Fimbriae play a role in cell surface hydrophobicity and attachment, probably by overcoming the initial electrostatic repulsion barrier that exists between the cell and substratum. A number of aquatic bacteria possess fimbriae, which have also been shown to be involved in bacterial attachment to animal cells.

Other cell surface properties may also facilitate attachment. Several studies have shown that treatment of adsorbed cells with proteolytic enzymes caused a marked release of attached bacteria, providing evidence for the role of proteins in attachment. The O antigen component of lipopolysaccharide (LPS) has also been shown to confer hydrophilic properties to gram-negative bacteria.

Agents of interest for the methods of the present invention are curcumin derivatives. As used herein the term refers to an agent that is a modified form of the curcumin structure, shown below, particularly dimethoxycurcumin (DMC), which structure is also shown below.

Many derivatives of curcumin are known in the art, and may be selected for use in the methods of the invention. For example, screening assays as described herein and exemplified in the Examples can find use in selection from known curcumin derivatives, which include, without limitation: dimethoxycurcumin, demethoxycurcumin, bisdemethoxycurcumin, bis-dehydroxy-curcumin; BDMC33 [2,6-bis(2,5-dimethoxybenzylidene)cyclohexanone]; (1E,4E)-1-(Thiophen-2-yl)-5-(2,6,6-trimethyl-cyclo-hex-1-en-1-yl)penta-1,4-dien-3-one; (1E,4E)-1-(2-Nitro-phen-yl)-5-(2,6,6-trimethyl-cyclo-hex-1-en-1-yl)penta-1,4-dien-3-one; (3E,5E)-3,5-Bis(2-chloro-benzyl-idene)-1-propyl-piperidin-4-one; (1E,4E)-1,5-Bis[2-(trifluoro-meth-yl)phen-yl]penta-1,4-dien-3-one; bis-dehydroxycurcumin carboxylic acid; curcuminoid bi- and tri-carbonylmethanes, e.g. N-phenylaminocarbonyl derivative of bis-demethoxycurcumin (CMC2.24) (Zhang et al. (2012) Curr. Med. Chem. 19(25): 4348-58); Tetrahydrocurcumin and quinoline derivatives thereof (Manjunatha et al. (2013) Food Chem 136(2):650-658); methoxylpolyethylene oxide-linked palmitate-modified curcumin (Amornwachirabodee et al. (2012) J. Pharm. Sci. 101(10):3779-86); curcumin-glucoside (Gadad et al. (2012) Curr. Pharm. Des. 18(1):76-84); (p-cymene)Ru(curcuminato)chloro; 2,6-bis(2,5-dimethoxybenzylidene)-cyclohexanone (BDMC33); 3,5-Bis(2-fluorobenzylidine)-4-piperidone; and the like.

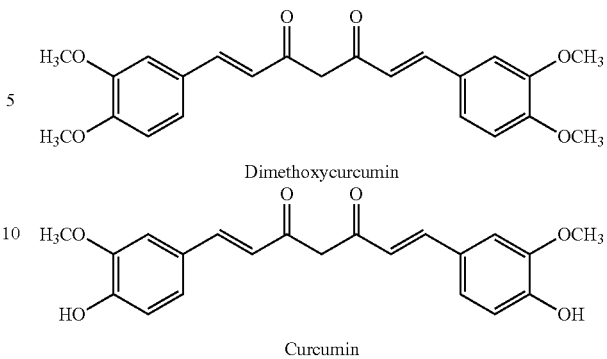

An effective dose of DMC may be a dose that achieves a concentration at the site of the biofilm of at least about 0.01 µM, at least about 0.1 µM, at least about 1 µM, at least about 5 µM, at least about 10 µM, at least about 50 µM, at least about 100 µM, at least about 500 µM, at least about 1 mM, at least about 5 mM, at least about 10 mM.

In some embodiments, the effective daily dose can range from about 0.5 mg to about 500 g, for example at least about 0.5 mg, at least about 1 mg, at least about 5 mg, at least about 10 mg, at least about 50 mg, at least about 100 mg, at least about 500 mg, at least about 1 g, at least about 5 g, at least about 10 g, at least about 50 g, at least about 100 g, and not more than about 500 g.

In some embodiments, the effective daily dose is provided in a unit dosage formulation in any increment. As non-limiting illustrative examples: administration of 5 g (e.g., one 1.6g capsule, two 800 mg capsules, etc.) can be performed twice in one day to deliver a daily dose of 3.2 g; or thrice in one day to deliver a daily dose of 4.8 g. As another non-limiting example, the use of 800 mg capsules facilitates any dose (e.g., a daily dose) with a multiple of (0.8 g) (e.g., 2.4 g, 3.2 g, 4 g, 4.8 g, 5.6 g, 6.4 g, etc.)

A treatment regime can entail administration daily (e.g., once, twice, thrice, etc. daily), every other day (e.g., once, twice, thrice, etc. every other day), semi-weekly, weekly, once every two weeks, once a month, etc. In another example, treatment can be given as a continuous infusion. Unit doses are usually administered on multiple occasions. Intervals can also be irregular as indicated by monitoring clinical symptoms. Alternatively, the unit dose can be administered as a sustained release formulation, in which case less frequent administration is required. Dosage and frequency may vary depending on the patient. It will be understood by one of skill in the art that such guidelines will be adjusted for localized administration, e.g. intranasal, inhalation, rectal, etc., or for systemic administration, e.g. oral, rectal (e.g., via enema), i.m. (intramuscular), i.p. (intraperitoneal), i.v. (intravenous), s.c. (subcutaneous), transurethrally, and the like.

The curcumin derivative can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of curcumin derivative includes use in combination with another therapeutic agent, e.g., a bacteriocidal or bacteriostatic agent. Therapeutic formulations can be prepared for storage by mixing the curcumin derivative with optional physiologically acceptable carriers, excipients or stabilizers (Remington's Pharmaceutical Sciences 16th edition, Osol, A. Ed. (1980)), in the form of lyophilized formulations or aqueous solutions. The curcumin derivative composition will be formulated, dosed, and administered in a fashion consistent with good medical practice. The "effective amount" of curcumin derivative to be administered will be governed by considerations such as those cited above (e.g., severity of disease etc.), and is the minimum amount necessary to prevent and/or reduce the targeted biofilm.

An active agent can be incorporated into a variety of formulations for therapeutic administration. For example, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In an exemplary embodiment, an active agent is formulated as a gel, as a solution, or in some other form suitable for intravaginal administration. In a further exemplary embodiment, an active agent is formulated as a gel, as a solution, or in some other form suitable for rectal (e.g., intrarectal) administration.

Screening Assays: Candidate agents, e.g. curcumin derivatives, may be screened for their ability to interfere with amyloid formation and biofilm formation. Inhibitors find use in the dissolution of biofilms. Assays to determine affinity and specificity of binding are known in the art, including competitive and non-competitive assays. Assays of interest include ELISA, RIA, flow cytometry, 96-well-based biofilm screens, etc. In one such example, biofilms of tester bacteria are grown in 96-well plates where they form biofilms on the plastic surface. Then, test compounds are added and the loss of biomass from the wells is quantified.

Generally a plurality of assay mixtures are run in parallel with different agent concentrations to obtain a differential response to the various concentrations. Typically, one of these concentrations serves as a negative control, i.e. at zero concentration or below the level of detection. The results in the absence (control) and presence of the agent are compared.

Conveniently, in these assays one or more of the molecules will be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule, which provides for detection, in accordance with known procedures.

In vitro binding assays may be provided in a wide variety of materials and shapes e.g. microtiter plate, microbead, dipstick, resin particle, etc. The substrate is chosen to minimize background and maximize signal to noise ratio. Binding may be quantitated by a variety of methods known in the art. After an incubation period sufficient to allow the binding to reach equilibrium, the insoluble support is washed, and the remaining label quantitated. Agents that interfere with binding will decrease the detected label.

Candidate agents include known and synthesized analogs of curcumin, for example including those set forth in Orlando et al. (2012) PLoS One. 7(3):e31869; Haukvik et al. (2011) Pharmazie. 66(1):69-74; and Ravindran et al. (2010) Biochem Pharmacol. 79(11):1658-66, each of which is specifically incorporated by reference. Natural or synthetically produced libraries and compounds are readily modified through conventional chemical, physical and biochemical means. Known pharmacological agents may be subjected to directed or random chemical modifications, such as acylation, alkylation, esterification, amidification, halogenation to produce structural analogs.

A variety of other reagents may be included in the screening assay. These include reagents like salts, neutral proteins, e.g. albumin, detergents, etc which may be used to facilitate optimal protein-DNA binding and/or reduce non-specific or background interactions. Also reagents that otherwise improve the efficiency of the assay, such as protease inhibitors, nuclease inhibitors, anti-microbial agents, etc. may be used.

Functional assays of interest include an assessment of the functional dissolution of microbial biofilms, e.g. as set forth in the examples.

Methods of Use

Formulations of biofilm inhibitors are administered to a host suffering from or predisposed to a microbial infection. Administration may be topical, localized or systemic, depending on the specific microorganism, preferably it will be localized. Generally the dose of biofilm inhibitor will be sufficient to decrease the microbial population in the biofilm by at least about 50%, usually by at least 1 log, and may be by 2 or more logs of release. The compounds of the present invention are administered at a dosage that reduces the microbial population while minimizing any side-effects. It is contemplated that the composition will be obtained and used under the guidance of a physician for in vivo use.

Biofilm inhibitors are also useful for in vitro formulations to dissolve microbial biofilms. For example, biofilm inhibitors may be added to hospital equipment, e.g. ventilation, water processing, etc.

The susceptibility of a particular microbe to biofilm inhibitors may be determined by in vitro testing, as detailed in the experimental section. Typically a culture of the microbe in the biofilm is combined with inhibitors at varying concentrations for a period of time sufficient to allow the protein to act, usually between about one hour and one day. The attached microbes are then counted, and the level of dissolution determined.

Virtually all microbes can participate in biofilms. Microbes of interest, include, but are not limited to: *Fusarium* sp., *Citrobacter* sp.; *Enterobacter* sp.; *Escherichia* sp., e.g. *E. coli*; *Klebsiella* sp.; *Morganella* sp.; *Proteus* sp.; *Providencia* sp.; *Salmonella* sp., e.g. *S. typhi, S. typhimurium; Serratia* sp.; *Shigella* sp.; *Pseudomonas* sp., e.g. *P. aeruginosa; Yersinia* sp., e.g. *Y. pestis, Y. pseudotuberculosis, Y enterocolitica; Franciscella* sp.; *Pasturella* sp.; *Vibrio* sp., e.g. *V. cholerae, V. parahemolyticus; Campylobacter* sp., e.g. *C. jejuni; Haemophilus* sp., e.g. *H. influenzae, H. ducreyi; Bordetella* sp., e.g. *B. pertussis, B. bronchiseptica, B. parapertussis; Brucella* sp., *Neisseria* sp., e.g. *N. gonorrhoeae, N. meningitidis*, etc. Other bacteria of interest include *Legionella* sp., e.g. *L.. pneumophila; Listeria* sp., e.g. *L. monocytogenes; Mycoplasma* sp., e.g. *M. hominis, M. pneumoniae; Mycobacterium* sp., e.g. *M. tuberculosis, M. leprae; Treponema* sp., e.g. *T. pallidum; Borrelia* sp., e.g. *B. burgdorferi; Leptospirae* sp.; *Rickettsia* sp., e.g. *R. rickettsii, R. typhi; Chlamydia* sp., e.g. *C. trachomatis, C. pneumoniae, Moraxella catarrhalis, Leptospira interrogans, C. psittaci; Helicobacter* sp., e.g. *H. pylori, Staphylococcus* sp., *Shigella* sp., *Streptococci* sp. etc.

Chronic infections remain a major challenge for the medical profession and are of great economic relevance because traditional antibiotic therapy is usually not sufficient to eradicate these infections. One major reason for persistence seems to be the capability of the bacteria to grow within biofilms that protects them from adverse environmental factors. Pseudomonas aeruginosa is not only an important opportunistic pathogen and causative agent of emerging nosocomial infections but can also be considered a model organism for the study of diverse bacterial mechanisms that contribute to bacterial persistence.

Dental plaque is the material that adheres to the teeth and consists of bacterial cells (mainly *Streptococcus mutans* and *Streptococcus sanguinis*), salivary polymers and bacterial extracellular products. Plaque is a biofilm on the surfaces of the teeth. This accumulation of microorganisms subject the teeth and gingival tissues to high concentrations of bacterial metabolites which results in dental disease.

*Legionella* bacteria are known to grow under certain conditions in biofilms, in which they are protected against disinfectants.

*Neisseria gonorrhoeae* is an exclusive human pathogen. Recent studies have demonstrated that it utilizes two distinct mechanisms for entry into human urethral and cervical epithelial cells involving different bacterial surface ligands and host receptors. In addition it has been demonstrated that the gonococcus can form biofilms on glass surfaces and over human cells.

Various methods for administration may be employed. The formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific biofilm inhibitor to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously.

Formulations

The curcumin derivatives can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, transurethral, etc., administration. The biofilm inhibitors may be systemic after administration or may be localized by the use of an implant or other formulation that acts to retain the active dose at the site of implantation.

The compounds of the present invention can be administered alone, in combination with each other, or they can be used in combination with other known compounds (e.g., antibiotics, etc.) In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing biofilm inhibitors is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 µg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, biofilm inhibitors may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Anti-mycotic agents are also useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin and rifampin.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

All publications, patents, and patent applications cited in this specification are herein incorporated by reference as if each individual publication, patent, or patent application were specifically and individually indicated to be incorporated by reference.

The present invention has been described in terms of particular embodiments found or proposed by the inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in methods, structures, and compounds without affecting the biological action in kind or amount. All such modifications are intended to be included within the scope of the appended claims.

Example 1

Curcumin and Dimethylated Curcumin Inhibit Amyloid-Mediated Adhesion and Amyloid-Integrated Biofilms Formed by E. Coli E. coli direct the assembly of functional amyloid fibers termed curli at the bacterial cell surface. Since the discovery of curli as adhesive fimbriae in 1989 and the identification of curli as amyloid in 2002, we now appreciate that functional amyloids are prevalent among microorganisms, e.g. Salmonella and Pseudomonas species, S. coelicolor, M. tuberculosis, and B. subtilis. The assembly of functional amyloids in microbes is regulated in order to direct polymerization at the right time and place, and to prevent toxicity. In this way, the formation of functional amyloids is juxtaposed to the undesired protein mis-assembly events and assembly of amyloidogenic protein oligomers and amyloid fibers associated with human diseases such as Alzheimer's disease. Curli assembly in E. coli requires the expression and proper interactions of several proteins encoded by the divergently transcribed csgBA and csgDEFG operons (csg, curli-specific genes). In vivo polymerization of the major curli subunit, CsgA, into β-sheet-rich amyloid fibers depends on the nucleating activity of the minor subunit, CsgB. CsgE, CsgF, and CsgG are assembly factors required for the stabilization and transport of CsgA and CsgB to the cell surface.

Curli are among the most-well studied microbial amyloid and have been ascribed roles in environmental persistence and transmission due to their ability to mediate adhesion to abiotic surfaces, such as stainless steel, and to biotic surfaces including plant leaves. Adhesion to both abiotic and biotic substrates can contribute to food-borne outbreaks by pathogenic strains such as E. coli O157:H7. Curli also promote cellular aggregation and serve as an adhesive scaffold to promote community behavior and biofilm assembly. Biofilms are multicellular communities characterized by a complex extracellular matrix that contribute to persistence in the host and the environment. Biofilm bacteria exhibit reduced sensitivity to antibiotics and cleansing agents. Commensal strains that colonize the gastrointestinal tract as well as strains that emerge as pathogens, such as uropathogenic E. coli (UPEC) when they egress from the GI tract into the urinary tract, commonly produce curli in vitro.

UPEC command much attention in the laboratory and the clinic due to the significant prevalence of urinary tract infection (UTI) caused by UPEC in the form of acute infections as well as chronic and recurrent infections that require long-term antibiotic therapy and are often associated with life-threatening sequelae that can include antibiotic resistance and sepsis. UPEC engage in a remarkable and well-studied genetic and molecular cascade to assemble type 1 and P pili, which are bonafide virulence factors associated with infections of the bladder and kidney, respectively. Yet, clinical isolates differ tremendously in their phenotypes in vitro and in vivo due to the myriad of other molecular features that differentiate them and their interactions with the host. Remarkably, the production of curli is prevalent among most uropathogenic E. coli strains. The coproduction of curli and cellulose enables the elaboration of bacterial biofilms formed on agar, at the air-liquid interface, and attached to PVC plastic. Recent in vivo studies provided evidence that curli provide a fitness advantage to UPEC as reflected in bladder and kidney bacterial titers in a mouse UTI model; and curli and cellulose modulate the immune response. Curli were also identified in human patient urine samples by electron microscopy and by antibody reactivity, indicating that curli are expressed in humans.

It is desirable to inhibit curli assembly and *E. coli* biofilm formation, as biofilms are implicated in most infectious diseases, and evidence is accumulating that bacterial amyloids contribute to environmental persistence and pathogenicity of uropathogenic and enterohemorrhagic organisms, e.g. *E. coli* and *Salmonella* species. Amyloid fibers have also recently been identified in the biofilms formed by the Gram-positive organism *Staphylococcus aureus*. Towards the goal of blocking microbial amyloid formation and biofilm formation, small-molecule inhibitors have been discovered that prevent the assembly of curli and thus prevent curli-integrated biofilms of *E. coli*. The antimicrobial peptide, LL-37, also inhibits curli formation. Other molecules prevent and disrupt the amyloid-integrated biofilms formed by the soil-dwelling organism *B. subtilis* in which the amyloid fibers are comprised of the TasA protein.

Described herein is the influence of curcumin and analogs thereof, particularly dimethylated curcumin (DMC), which block curli-mediated adhesion and inhibit curli-integrated biofilm formation by uropathogenic *E. coli*. Curcumin does not affect the production of curli proteins, assessed by Western blot analysis. Thus, curcumin influences curli post-translationally and inhibits curli-dependent biofilm formation. Furthermore, we demonstrate that DMC exhibits superior biofilm inhibition properties as compared to curcumin.

Results

Curcumin blocks curli-mediated adhesion to fibronectin, but does not influence curli protein expression. We employed a commonly used fibronectin-binding assay to determine whether curcumin blocks adhesion of *E. coli* strain MC4100 to fibronectin-coated plates. MC4100 is the *E. coli* strain in which curli biogenesis was first described. It is a traditionally used laboratory K12 strain that expresses curli but produces neither cellulose, a major *E. coli* biofilm determinant, nor type 1 pili; it does not form appreciable biofilm on glass, plastic, or at an air-liquid interface. UTI89, on the other hand, is a prototypical biofilm-competent strain that forms biofilms on agar, on plastic, and at an air-liquid interface when expressing curli and cellulose. Since curli are sufficient to mediate binding to fibronectin, the use of MC4100 readily allows one to determine whether a compound or external stimulus can influence curli-dependent adhesion. In a dose-dependent manner, bacteria growing under normal curli-producing conditions on agar in the presence of curcumin exhibited reduced adhesion to the protein fibronectin (FIG. 1A). As demonstrated in FIG. 1B, curcumin did not influence the production of curli proteins. These results suggest that curcumin binds to curli and results in decreased curli-mediated adhesion to fibronectin.

Figure 2:
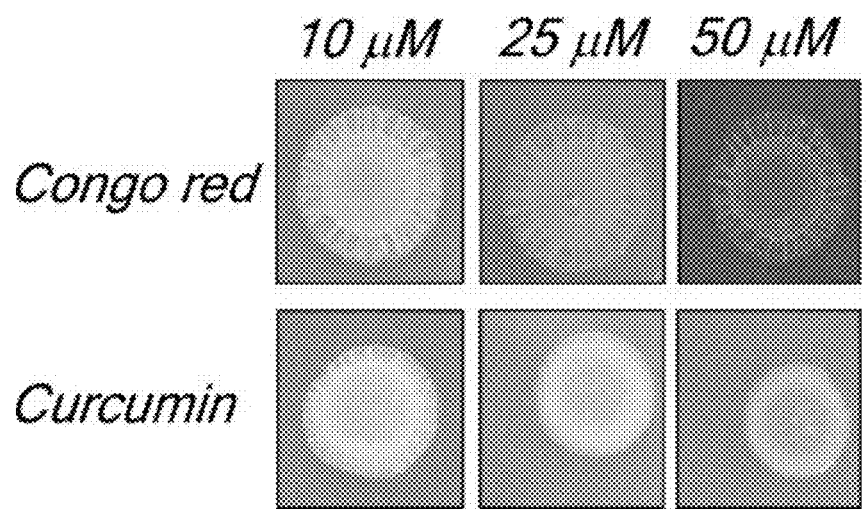
FIGS. 2A-2C. Curcumin blocks biofilm formation on agar, at the air-liquid interface, and attached to plastic. Congo red is often used to dye and visualize better the red, drough, and dry(rdar) phenotype associated with curli and cellulose, and does not block biofilm formation by UTI89 (A, top). Curcumin added to YESCA nutrient agar inhibits the hallmark colony morphology associated with UTI89 biofilm formation (A, bottom). Curcumin, but not Congo red, blocks UTI89 biofilm formation at the air-liquid interface (B). Curcumin also blocks the ability of UTI89 to form a biofilm associated with PVC plastic in a 96-well crystal violet assay (C).
Figure 2:
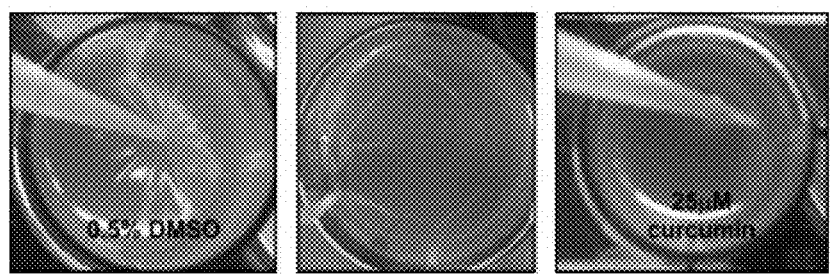
Figure 2:
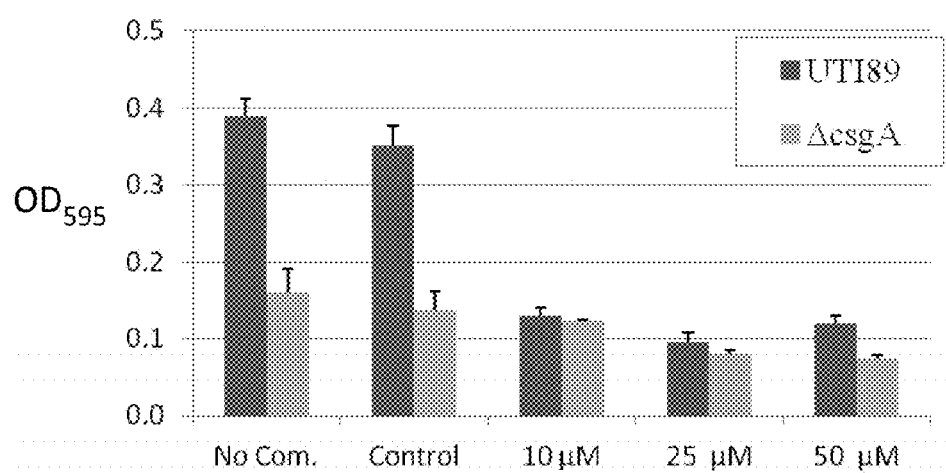

Curcumin blocks biofilm formation on agar, at the air-liquid interface, and attached to plastic. In the presence of curcumin, UTI89 grown on agar plate lost the hallmark rough and wrinkled phenotype and showed the smooth and non-wrinkled morphology similar to MC4100, the non-biofilm former (FIG. 2A). Western blot analysis confirmed that curli production was not affected as demonstrated for MC4100 in FIG. 1. Curcumin was able to completely prevent pellicle formation (FIG. 2B) and plastic-associated biofilm formation was prevented in the lowest concentration of curumin tested, at 10 µM.

Figure 3:
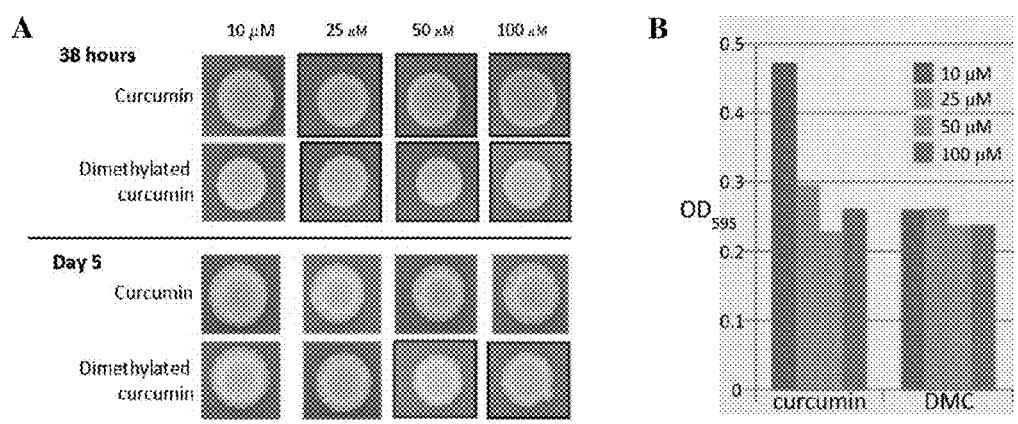
FIGS. 3A-3B. DMC is more potent than curcumin in blocking biofilm formation on agar and maintains its efficacy even after 5 days in agar (A). DMC is effective at preventing biofilm formation attached to plastic at a lower concentration (10 µM) than that required for curcumin-mediated inhibition (25 µM) (B).

Dimethyl curcumin, a curcumin analog, blocks biofilm formation on agar, at the air-liquid interface, and attached to plastic. We performed the same biofilm assays as were performed on curcumin with a curcumin analog that is commercially available, DMC. Results comparing curcumin and DMC revealed that DMC was more potent at inhibiting biofilm on agar, and exhibited its influence even out to 5 days of bacterial growth, whereas biofilm inhibition in the presence of curcumin was diminished after 5 days (FIG. 3A). This suggests that DMC may exhibit enhanced stability and thus maintain its efficacy after five days. DMC was also more potent at blocking biofilm formation at the air-liquid interface and prevented the formation of a biofilm at concentrations as low as 10 µM, whereas 25 µM curcumin was required for complete inhibition of formation of a biofilm at the air-liquid interface for UTI89. Similarly, DMC blocked UTI89 biofilm attached to PVC at 10 µM, whereas 25 µM curcumin was required to inhibit plastic-associated biofilm formation.

Figure 4:
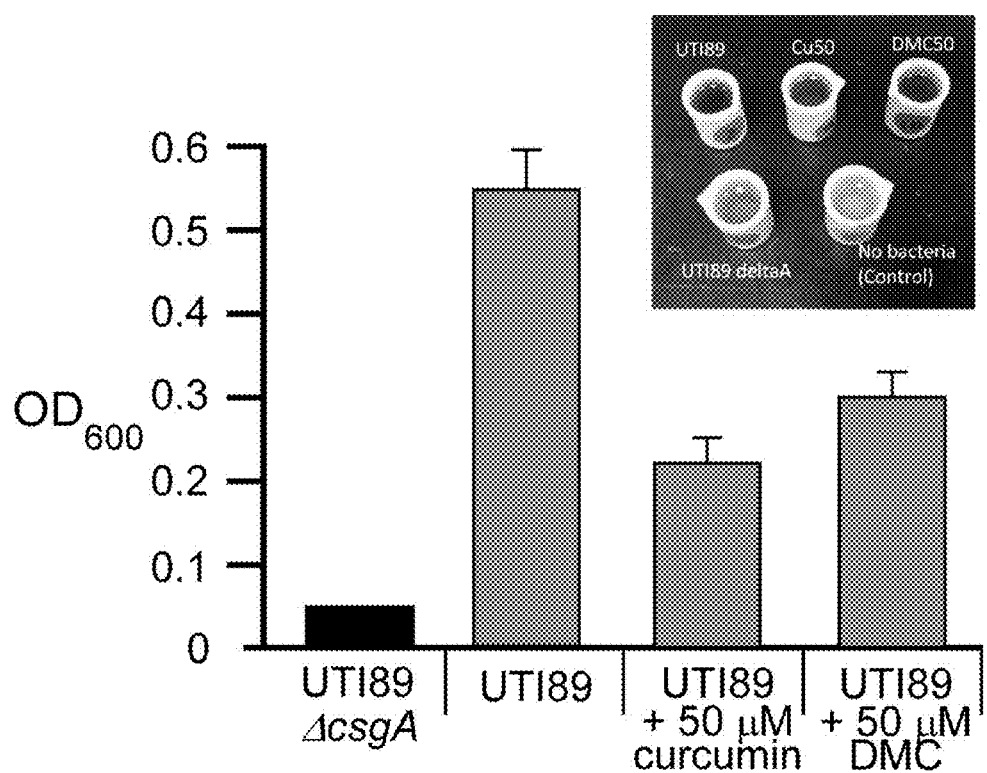
FIG. 4. Curcumin and dim ethyl curcumin reduce E. coli biofilm formation attached to Teflon using 1 mL Teflon beakers. After bacterial incubation for 48 hours at 26° C. in YESCA nutrient broth in the presence or absence of compounds, planktonic and loosely associated bacteria were washed from the beakers and adherent bacteria were stained with crystal violet, dissolved in ethanol and quantified by spectrophotometry.

Teflon is often used as a material in various industrial and biomedical applications, including the production of catheters. Teflon is often employed due to its general anti-adherent properties. Yet, even *E. coli* can adhere to Teflon and forms biofilms on Teflon surfaces. Thus, we also examined the ability of curcumin and DMC to prevent biofilm formation attached to Teflon using small 1-mL Teflon beakers. As demonstrated in FIG. 4, both curcumin and DMC were effective at significantly preventing biofilm formation attached to Teflon.

Mode of action of curcumin in preventing biofilm formation. Together, the data are consistent with curcumin binding to curli (as has been demonstrated in McCrate, Zhou, and Cegelski, Chemical Communications 2013, 49:4193-4195), and preventing interactions between curli and other components of the extracellular matrix, particularly the polysaccharide component. Thus, the activity of curcumin reveals that it is possible for bacteria to secrete major biofilm components, but still have biofilm formation prevented.

Discussion

Curcumin has been shown to bind to the amyloid protein, amyloid β, in oligomer form and fibril form (Yang et al. Curcumin Inhibits Formation of Amyloid β Oligomers and Fibrils, Binds Plaques, and Reduces Amyloid in Vivo THE JOURNAL OF BIOLOGICAL CHEMISTRY. Vol. 280, No. 7, Issue of Feb. 18, 2005 pp. 5892-5901,). Regarding amyloid b, curcumin was also shown to prevent amyloid fibril formation in vitro (Ono et al. Curcumin has potent anti-amyloidogenic effects for Alzheimer's β-amyloid fibrils in vitro. Journal of Neuroscience Research Volume 75, Issue 6, pages 742-750, 2004), which differs from curcumin-mediated inhibition of biofilms, in which curli fibers are still produced, but curcumin blocks their ability to mediate biofilm formation.

The influence of curcumin on adhesion and biofilm formation by uropathogenic *E. coli* (UPEC) and bacterial amyloid fibers or amyloid-mediated adhesion or amyloid-integrated biofilm formation is novel. Also, DMC is more effective than curcumin and may exhibit enhanced stability giving it superior administrative and bioavailability properties to curcumin. These compounds have no influence on cell viability in UPEC and so can be used as an anti-virulence strategy to block adhesion and biofilm formation without targeting cell viability as a classic antibiotic would. This is an attractive approach that prevents the overwhelming alteration to the microbial balance that is typically ascribed to traditional antibiotics and may be associated with reduced prevalence of antibiotic resistance.

In specific example, the methods of the invention find use preventing and treating urinary infections, including infections of the bladder and kidney as well as catheter-associated urinary tract infections. The methods are also useful in preventing *E. coli* contamination of food processing plants due to curli-producing organisms such as *E. coli* 0157:H7 and *Salmonella* species. Additionally, the methods of the invention find use in blocking amyloid-mediated adhesion and amyloid-integrated biofilm formation by other amyloid-producing organisms. The curcumin compounds are able to bind to curli extracellularly and inhibit biofilm extracellularly and therefore do not have to enter bacterial cells and are not subject to resistance mechanisms such as small-molecule efflux systems.

Materials and Methods

Growth conditions. UTI89, UTI89ΔcsgA, MC4100, and MC4100Δcsg were grown on YESCA (0.5 g/L yeast extract; 10 g/L Casamino acids) agar supplemented with additional compounds as indicated.

Western blot analysis. The cell-associated curli proteins, CsgA and CsgG, were examined by immunoblot assays as described (41). Briefly, whole-cell samples with equivalent cell number were prepared as cell pellets of 1 mL cell culture with an $OD_{600}$ of 1.0. Each pellet was treated with 100 μL hexafluoroisopropanol (HFIP) to dissociate curli subunits (41). HFIP was removed by vacuum centrifugation, and samples were resuspended in SDS-PAGE loading buffer. Protein gel electrophoresis was carried out using 12% SDS-PAGE gels (Invitrogen) and blotted onto 0.2 mm nitrocellulose transfer membranes (Whatman). The polyclonal rabbit antiserum to CsgA or CsgG was used as the primary antibody and horseradish peroxidase (HRP) conjugated goat anti-rabbit antibody (Pierce) was used as the secondary antibody (55).

Biofilm assays. Colony biofilm formation was initiated by spotting 10 μl of overnight bacterial culture onto a YESCA agar plate (Kolodkin-Gal et al. (2010) Science 328:627-629). Colony morphology was observed after designated growth times at 26° C. Biofilm in YESCA broth attached to plastic (polyvinyl chloride, PVC) was determined using the Kolter crystal violet assay as described by O'Toole et al. (1998) Mol. Microbiol. 28:449-461. Briefly, bacterial cells were grown in 96-well PVC plates; unattached cells were washed away; and cells remaining associated with the PVC wells were stained with 0.1% crystal violet. The extent of biofilm formation was quantified by measuring the absorbance of crystal violet at $OD_{595}$ after dissolving the PVC-associated biomass in 95% ethanol. The percent biofilm represents the increase in biofilm formation in the presence of various concentrations of DMSO and ethanol relative to biofilm formation when no compound was present. The mean of triplicate individual experiments was used and error bars represent the standard deviation. Pellicle formation was initiated by inoculating 4 μL of an overnight bacterial culture grown in YESCA broth in 4 mL YESCA in 12-well-plate wells and incubated at 26° C. Pellicle formation was inspected visually and assessed by perturbation with a pipet tip after 72 hours of growth.

What is claimed is:

1. A method of inhibiting microbial biofilm maintenance or formation, the method consisting of:
   contacting microbes involved in said biofilm formation or maintenance with an effective dose of dimethoxycurcumin (1, 7-bis(3, 4-dimethoxyphenyl)-1, 6-heptadiene-3, 5-dione), wherein the effective dose provides for a concentration at the biofilm site of from about 0.01 μM to about 10 mM.

2. The method of claim 1, wherein said biofilm is present in vitro.

3. The method of claim 1, wherein said biofilm is present in vivo.

4. The method of claim 1, wherein the biofilm comprises *E. coli*.

5. The method of claim 1, wherein the biofilm comprises uropathogenic or enterohemorrhagic microorganisms.

6. The method of claim 4, wherein the biofilm comprises uropathogenic *E. coli*.

7. The method of claim 3, wherein an effective daily dose ranges from about 0.5 mg to about 500 g.

8. The method according to claim 1, further comprising contacting microbes involved in said biofilm formation or maintenance with an effective dose of a bactericidal agent in combination with said dimethoxycurcumin.

9. The method of claim 1, wherein the dimethoxycurcumin inhibits biofilm extracellularly.

10. The method of claim 3, wherein the biofilm is present in a human individual.

* * * * *